United States Patent [19]

Eibl

[11] Patent Number: 4,837,023
[45] Date of Patent: Jun. 6, 1989

[54] COMPOSITIONS CONTAINING HEXADECYLOPHOSPHOCHOLINE AND ALKYLGLYCEROLS AND USES THEREOF

[75] Inventor: Hansjörg Eibl, Bovenden, Fed. Rep. of Germany

[73] Assignee: Max-Planck-Gesellschaft Zur Foederung der Wissenschaften, Goettingen, Fed. Rep. of Germany

[21] Appl. No.: 97,960

[22] PCT Filed: Dec. 4, 1986

[86] PCT No.: PCT/EP86/00705

§ 371 Date: Oct. 2, 1987

§ 102(e) Date: Oct. 2, 1987

[87] PCT Pub. No.: WO87/03480

PCT Pub. Date: Jun. 18, 1987

[30] Foreign Application Priority Data

Dec. 4, 1985 [DE] Fed. Rep. of Germany ....... 3542893
Feb. 28, 1986 [DE] Fed. Rep. of Germany ....... 3606631

[51] Int. Cl.$^4$ .................... A61K 9/10; A61K 31/685; C07F 9/09
[52] U.S. Cl. ..................................... 424/439; 514/77; 424/400
[58] Field of Search ........................... 514/77; 424/439

[56] References Cited

FOREIGN PATENT DOCUMENTS 0108565 of 0000 European Pat. Off. .
0123850 of 0000 European Pat. Off. .

OTHER PUBLICATIONS

Unger, et al., Klin. Wochenstr. 63: 565–571 (1985).
Ando, et al., Cancer. Res. 32: 125–129 (1972).
Eibl, et al., Canc. Res. Clin. Oncol. 111 (suppl) 1986.
Eibl, et al., J. Clin. Res. Clin. Oncol 111(suppl) 1986, abstracts Ncy 21 and Ncy 22.
Bekemer, et al., Agents & Actions 11(6/7): 565–564 (1981).
Zeller, et al., "Dialog Abstract".
Croft et al, The activity of alkyl phosphoryl cholines and related derivatives against leishmania donovani. CA107 (19): 168296c.

Primary Examiner—William R. Dixon, Jr.
Assistant Examiner—David M. Brunsman
Attorney, Agent, or Firm—Felfe & Lynch

[57] ABSTRACT

Cytotoxically-effective medicaments containing hexadecylphosphocholine as active material.

13 Claims, No Drawings

COMPOSITIONS CONTAINING HEXADECYLOPHOSPHOCHOLINE AND ALKYLGLYCEROLS AND USES THEREOF

Hexadecylphosphocholine is a known substance. In Pharmazie 37, 1982, pages 706-707, a lysing and fusogenic action is stated herefor. It has now been found that this compound also possesses an excellent anti-tumour action and, in comparison with homologous compounds, which are described in European Application 108 565, is characterized by the following surprising properties: whereas similar compounds with a shorter alkyl radical, such as for example tetradecylphosphocholine, show practically no anti-tumour action (for example, in vitro in the L1210 colony experiment or in vivo on the autochthanous methylnitrosourea-induced mammary carcinoma of the rat), those with a longer alkyl radical, such as for example octadecylphosphocholine, are admittedly anti-tumour effective but, at the same time, far too toxic and, therefore, not usable as medicaments. Thus, for example, in the case of a determination of the subacute toxicity during a treatment of 5 weeks at an anti-tumour effective daily dose of 77 $\mu$mole/kg. rat orally, there was obtained an extremely high mortality which was 80% of all animals. Therefore, in spite of an anti-tumour action, the median survival time in comparison with the control was shortened by 72% in the case of octadecylphosphocholine-treated animals. In comparison thereto, in the case of hexadecylphosphocholine-treated animals, the mortality was lower by a half and, as a result of the absence of a chronic toxicity, it resulted in a highly significant increase of the median survival time of 26% in comparison with the controls.

Thus, within the homologous alkyl compounds, hexadecylphosphocholine occupies a surprising special position in that only heaxadecylphosphocholine possesses a practically useful good anti-tumour action. Homologues with shorter alkyl radicals possess no or a much too low anti-tumour action. Homologues with longer alkyl radicals are admittedly effective against tumours but, at the same time, are much too toxic. Therefore, only hexadecylphosphocholine displays a sufficient anti-tumour action in non-toxic doses.

The invention concerns medicaments which contain hexadecylphosphocholine as active material and are especially suitable for the treatment of tumours.

Such medicaments possess an outstanding cytotoxic effectiveness which was demonstrated not only in vivo on chemically-induced mammary carcinoma of the rat but also in vitro on leukaemia cells in the cell culture. Furthermore, in a clinical pilot study in the case of female patients with mammary carcinomas, skin metastases were completely healed in the case of topical use.

It is known that hitherto no medicament for the treatment of tumours, especially of malignant tumours, was available which was satisfactory in all respects. Thus, for example, for the topical treatment of skin metastases in patients with metastasing tumours, at present only 5-fluorouracil is available. Further developments of other cytostatics have hitherto not progressed to clinical maturity for this manner of administration. On the other hand, from a clinical point of view, such a concept of palliative therapeutic use is especially desirable since alternative concepts of treatment, such as surgical measures, radiation therapy and systemic chemotherapy, constitute comparatively aggressive therapy modalities.

Furthermore, a considerable number of patients are available as potential treatment candidates for such a topical treatment. Thus, e.g. the proportion of mammary carcinoma patients who display a skin attack amount to about 25 to 35%.

The prerequisite for topical treatment on the part of the active material to be used are compatibility to the skin, cytotoxic effectiveness against tumour cells and sufficiently deep penetration.

Therefore, the object of the invention is, in the first place, to provide a medicament which is suitable for the topical treatment of tumours. A further object of the invention is, in addition, also to provide, in general, a medicament usable in other forms of administration which combines a good effectiveness against tumours with low toxicity and is, therefore, generally usable in tumour therapy.

According to the invention, these objects are solved by a medicament which is characterised in that it contains hexadecylphosphocholine as active material.

Especially for topical administration but also for the preparation as medicaments for other modes of administration, it has proved to be especially advantageous to use the hexadecylphosphocholine together with at least one alkylglycerol with 3 to 12 carbon atoms in the alkyl radical which can be present attached in the form of an ether group to one of the primary or secondary OH groups of the glycerol. Such alkylglycerols increase or improve the action of the hexadecylphosphocholine synergistically. There are hereby preferably used alkylglycerols with 3 to 9 C-atoms alone or as mixture.

Therefore, a synergistically-acting medicament which contains
(a) hexadecylphosphocholine and
(b) an alkyl glycerol of the general formula I

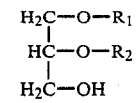

in which one of the radicals $R_1$ and $R_2$ signifies an alkyl group with 2 to 12 C-atoms and the other radical an H-atom, as well as possibly further usual phaarmacological additive and diluent materials, possesses especially favourable actions.

Such a mixture is, in the following, also called a cascade.

The content of hexadecylphosphocholine in mg./ml. of cascade is indicated by a subsequent index in such a manner that, for example, a cascade mixture which contains 5 mg./ml. of hexadecylphosphocholine is described as cascade$_5$, a mixture with 200 mg. of hexadecylphosphocholine per ml. of cascade as cascade$_{200}$.

The preparation of alkylglycerols is known, for example, from DE-OS No. 33 43 530.8.

Alkylglycerol-water mixtures which contain, for example, nonylglycerol, octylglycerol, hexylglycerol, pentylglycerol, propylglycerol and ethylglycerol, are preferred. Such aqueous mixtures preferably contain 3 of the said glycerol ethers, namely, a lower one (ethyl, propyl), a medium one (pentyl, hexyl) and a higher one (nonyl, octyl), whereby the amount by weight of the lower ether is about as great as the sum of amounts by weight of the two other glycerol ethers. The amount of water is about equal to the amount of the lower glycerol ether and amounts, for example, to half of the total amount of glycerol ethers present. Examples of such glycerol ether-water mixtures are set out in the following:

|  | water | glycerol propyl ether | glycerol hexyl ether | glycerol nonyl ether |
| --- | --- | --- | --- | --- |
| parts by weight | 2 | 2 | 1 | 1 |

|  | water | glycerol ethyl ether | glycerol pentyl ether | glycerol octyl ether |
| --- | --- | --- | --- | --- |
| parts by weight | 2 | 2 | 1 | 1 |

The medicaments according to the invention are suitable to a special degree for topical administration. In order to treat skin tumours or skin metastases with this medicament, the skin regions in question are rubbed in two or three times daily with cascade$_5$ to cascade$_{200}$. Harmful side effects have hitherto not been observed, not even in the case of patients who have been treated over a period of time of 3 months. The remission of the skin metastases is accompanied by a normalisation of the skin, as could clearly be demonstrated by tissue sections. Several patients with skin metastases were treated in this way and a complete disappearance of the mammary carcinoma skin metastases hereby observed.

The topical treatment with the preferred agent according to the invention in the formulation cascade$_5$ to cascade$_{200}$ can also be used for the treatment of internal tumours or metastases by rubbing into large areas of the skin. Therapeutically effective blood levels are hereby achieved by resorption through the skin. An advantage of this mode of administration lies in the fact that the preparations cascade$_5$ to cascade$_{200}$ are tolerated by the skin without problems.

This preferred type of preparation of the medicament according to the invention in the form of solutions of cascade$_5$ to cascade$_{200}$ is also well suited for the preparation of suppositories for rectal insertion. Internal tumours or internal metastases can also be readily treated in this way.

Another form of use of the medicaments according to the invention consists in the instillation into preformed body cavities. This mode of administration is especially suitable for pleural carcinoses, malign ascites, malign pericardial discharges and bladder carcinomas. In this case, the hexadecylphosphocholine is used either alone or in combination with usual carrier and dilution agents, especially also with cascades.

For systematic administration, there comes into consideration, for example, oral or intravenous administration.

For oral administration, hexadecylphosphocholine is used, for example, in the form of a drinking solution. As carriers there are suitable, for example, milk, cocoa, fruit juice or drinking water. The preparation of such a drinking solution takes place, for example, by dilution of a concentrated alcoholic solution of hexadecylphosphocholine with water or another of the previously mentioned agents. In the case of rats, daily doses of 20, 40 and 60 mg./kg. body weight of hexadecylphosphocholine led to a complete remission of chemically induced mammary carcinomas. Hexadecylphosphocholine hereby proved to be better effective and better compatible than, for example 1-octadecyl-2-methyl-rac-glycero-3-phosphocholine. In the case of the tumour model used for these experiments, it is a question of a so-called hard model. This means that findings obtained with this model can also be transmitted to the human situation.

For the intravenous administration via the intravenous infusion therapy, the hexadecylphosphocholine is expediently used in physiological common salt solution. Other infusion solutions can hereby also be used. The dosage on humans for such solutions is, for example, 1–10 mg./kg. of body weight.

Finally, several forms of administration of the medicament according to the invention can be used combined, whereby the especial topic compatibility has the result that, on the one hand, a rubbing in of the skin can be combined with one of the other forms of administration.

A further carrier mixture for hexadecylphosphocholine which has proved to be especially useful consists of a mixture of about 4 parts by weight of water, 4 parts by weight of propylglycerol and 2 parts by weight of each of hexylglycerol and nonylglycerol.

The topical use of the medicament according to the invention in the especially preferred form of preparation of cascade$_5$ to cascade$_{200}$ over a period of time of several months shows that the local toxicity is limited to an increased desquamation of the skin, similarly to the local use of acetylsalicylic acid.

Thus, the invention makes available a new medicament for the treatment of tumours and hereby provides not only a further anti-tumour agent but also provides, for the first time, an agent which has also been shown to be effective in the case of topical administration in clinical experiments. New possibilities for the treatment of tumour patients are hereby opened up.

For the preparation of appropriate medicaments, hexadecylphosphocholine is worked up with conventional pharmaceutical carrier materials and/or dilution agents or other adjuvant materials to pharmaceutical compositions or is brought into a therapeutically usable form. This takes place, for example, in that the hexadecylphosphocholine is mixed or homogenised together with usual carrier and/or dilution or adjuvant materials at temperatures between 20° and 120° C., preferably 30°–100° C., the so obtained mixture is, for the preparation of compositions which contain 5 to 2000 mg., preferably 10 to 500 mg. and especially 30 to 400 mg. hexadecylphosphocholine, poured into hollow cells of appropriate size or filled into capsules of appropriate size or granulated and the pressed into tablets, possibly with the addition of further usual adjuvant materials.

For example, in that one mixes hexadecylphosphocholine with one or more of the following materials: starch, cellulose, lactose, formalin-casein, modified starch, magnesium stearate, calcium hydrogen phosphate, highly dispersed silicic acid, talc, phenoxyethanol, granulates the mixture obtained, possibly with an aqueous solution which, as component, contains at least gelatine, starch, polyvinylpyrrolidone, vinylpyrrolidonevinyl acetate co-polymer and/or polyoxyethylsorbitan monooleate, homogenises the granulate possibly with one or more of the above-mentioned adjuvant materials and presses this mixture to tablets or fills into capsules, whereby such tablets or capsules in each case contain 5 to 2000 mg. hexadecylphosphocholine, or that, after the addition of soya lecithin, as well as possibly of 0.1–0.5 parts by weight of phenoxyethanol (referred to one part by weight of hexadecylphospholine), suspends hexadecylphosphocholine at temperatures between 33°-37° C. in molten hard fat and homogenises and subsequently pours the mixture into hollow cells, whereby the dosage unit contains 5 to 2000 mg. hexadecylphosphocholine, as well as possibly 0.1-0.5 parts by weight of phenoxyethanol (referred to one part by weight of hexadecylphosphocholine), or in that one homogenises hexadecylphosphocholine at a temperature between 50° and 120° C., preferably 50° to 100° C., possibly in the presence of one or more emulsifiers and/or 0.1-0.5 parts by weight of phenoxyethanol (referred to one part by weight of hexadecylphosphocholine) with at least one of the following materials: paraffin, vaseline, aliphatic alcohol with 12 to 25 C-atoms, aliphatic monocarboxylic acid with 15 to 20 C-atoms, sorbitan monopalmitate, polyoxyethylenepolyol fatty acid ester, and emulsifies the mixture obtained between 50° and 120° C. with water, possibly with the addition of a polyhydroxy lower aliphatic alcohol and/or phenoxyethanol; or in that one dissolves hexadecylphosphocholine in water or vegetable oil, possibly in the presence of 0.1-0.5 parts by weight of phenoxyethanol (referred to one part by weight of hexadecylphosphocholine), as well as possibly in the presence of an emulsifier, at temperatures between 30°-100° C., and possibly makes up the so obtained solution with so much water or vegetable oil that the final solution contains 0.05 to 10 percent by weight, preferably 0.1 to 5 percent by weight, of hexadecylphosphocholine.

As emulsifiers, there come into question, for example: non-ionic emulsifiers, as well as ionic emulsifiers. In the case of non-ionic emulsifiers, it is a question of, for example, triglyceride mixtures of saturated vegetable fatty acids with $C_8$, $C_{10}$ and $C_{12}$ or of emulsifiers based on polyaddition products of ethylene oxide, such as, for example, alkyl- and acyl-substituted polyaddition products of ethylene oxide, polyethyleneglycol fatty acid esters, reaction products of ethylene oxide with castor oil, esters of hydrogenated castor oil fatty acids with oxyethylated glycerol. Furthermore, it can be a question of emulsifiers based on fatty acid amides or fatty acid condensation products with hydrophilic groups. As ionic emulsifiers, there come into question, for example, emulsifiers based on fatty acid monoesters of glycerol or of other polyhydroxy alcohols (Lunacera alba).

If, in the case of the above-given preparation of the medicaments, the hexadecylphosphocholine is used in the presence of a glycerol ether of formula I or of a mixture of such glycerol ethers of formula I, there is observed a synergistic action increase of the anti-tumour action.

For this purpose, the hexadecylphosphocholine is used with 1 to 30, preferably 2 to 20 parts by weight (referred in each case to one part by weight of hexadecylphosphocholine) of at least one glycerol ether of formula I or a mixture of such glycerol ethers, as well as possibly 0.5-30, preferably 1-20 parts by weight of water (also referred to one part by weight of hexadecylphosphocholine). This mixing with the glycerol ethers can take place initially in the preparation of the appropriate medicaments but possibly also at a later stage of preparation.

Hexadecylphosphocholine shows, for example, a good action on 7,12-dimethylbenzanthracene-induced mammary carcinoma of the rat; as well as on methylnitrosourea-induced mammary carcinoma of the rat.

For example, in the case of the above-mentioned experimental method, at a dose of 10 mg./kg. body weight of rat, there is achieved a cessation of growth of the tumours, at higher doses also a complete disappearance of the growths.

The lowest already effective dose in the above-mentioned animal experiment is, for example 5 mg./kg. orally
5 mg./kg. intravenously.

As general dose range for the action (animal experiment as above), there comes into question, for example:

5-50 mg./kg. orally, especially 15-32 mg./kg.
5-50 mg./kg. intravenously, especially 15-32 mg./kg.

The direction of action of the compounds according to the invention is comparable with the action of the known medicament active material TAMOXIFEN but, in this regard, there exist the following differences: The action is stronger and of longer duration than that of TAMOXIFEN.

Indications for which the compounds of the invention come into consideration: mammary cancer and other kinds of human cancer.

The pharmaceutical compositions contain, in general, between 5-2000 mg., for example 10-400 mg. of hexadecylphosphocholine.

The administration can take place, for example, in the form of tablets, capsules, pills, dragees, cones, salves, gels, creams, powders, dusting powders, aerosols or in liquid form. As liquid forms of use, there come into question, for example: oily or alcoholic or aqueous solutions, as well as suspensions and emulsions. Preferred forms of use are tablets which contain between 0.1% to 5% of active substance.

The individual dose of hexadecylphosphocholine can, for example, lie
(a) in the case of oral medicinal forms between 5-100 mg./kg. body weight, preferably 15-50 mg./kg. body weight,
(b) in the case of parenteral medicinal forms (for example intravenous, intramuscular) between 5-100 m./kg. body weight,
(c) in the case of medicinal forms for local administration to the skin or mucous membranes (for example in the form of solutions, lotions, emulsions, salves and so forth) between 50-2000 mg., preferably 80-1500 mg.

For example, 1 tablet with a content of 40-400 mg. of active substance can be recommended 3 times daily or, for example, in the case of intravenous injection, 1-5 times daily an ampoule of 1-5 ml. content with 50-250 mg. of substance. In the case of oral administration, the minimum daily dose lies, for example, at 120 mg.; the maximum daily dose in the case of oral administration is not to lie above 100 mg./kg.

The acute toxicity of hexadecylphosphocholine in the mouse (expressed by the LD 50 mg./kg.; method according to Miller and Tainter, Proc. Soc., Exper. Biol. a. Med. 57 (1944) 261) lies, for example, in the case of oral administration, between 200 and 450 mg./kg. body weight.

The medicaments can be used in human medicine, in veterinary medicine, as well as in agriculture, alone or in admixture with other pharmaceutically active materials.

The invention is explained by the following Examples.

EXAMPLE 1

Preparation of hexadecylphosphocholine.H₂O (a) Hexadecylphosphoethanolamine (phosphorylation, ring closure and ring opening)

Hexadecanol (1 mole, 243 g.) and triethylamine (1.8 mole, 180 g.) are dissolved in 1.5 l. THF (tetrahydrofuran) and added dropwise to a vigorously stirred solution of phosphorus oxychloride (1.2 mole, 184 g.) in 120 ml. THF in such a manner that the temperature in the reaction vessel (three-necked, 5 l., with dropping funnel, thermometer and stirrer) does not exceed 10° C. For the acceleration of the procedure, the reaction vessel is cooled with an ice-salt mixture. Immediately after the dropping in, the reaction is terminated (detection via TLC in ether: Rf values of 0.8 for the starting product, of 0.0 for the reaction product after hydrolysis with water).

One removes the ice bath and drops into the reaction mixture, with vigorous stirring, a solution of ethanolamine (1.5 mole, 92 g.) and triethylamine (1.8 mole, 180 g.) in 1 l. dioxan in such a manner that the temperature in the reaction vessel increases to 65° to 70° C. The ring formation is then concluded (detection by TLC in ether: Rf value of 0.2). One filters off from precipitated triethylamine hydrochloride while still warm and mixes the filtrate at 40° to 50° C. with 1.5 l. 2N formic acid. After 15 minutes, the ring opening is concluded (detection of TLC in ether: Rf value 0.0; TLC in chloroform/methanol/acetic acid/water 100:60:20:5 in vol.: Rf value 0.8). One cools to $-20°$ C., filters off the precipitate which consists substantially of pure hexadecylphosphoethanolamine. In the case of slight impurities, a chromatographic purification is carried out (see Example 2). Microanalysis (M.W. 365.50):

|  | C | H | N | P |
|---|---|---|---|---|
| calc. (%): | 59.15 | 11.03 | 3.83 | 8.48 |
| found (%): | 59.01 | 10.95 | 3.79 | 8.31 |

(b) (Methylation of 1)

The crystals obtained according to Example 1 are, without further purification, taken up in 1.2 l. 2-propanol and 0.4 l. dichloromethane. One mixes the suspension of the crystals, with vigorous stirring, with potassium carbonate (4 mole, 560 g.) in 1 l. of water. The two-phase reaction mixture is mixed dropwise and while stirring with dimethyl sulphate (4 mole, 500 g.) in such a manner that the temperature does not exceed 40° C. The reaction is ended 60 minutes after the dropping in (detection by TLC in chloroform/methanol/25% ammonia 59:50:5 in vol.; Rf value 0.3). After phase separation at 20° C., the upper phase contains the product. One removes the solvent on a rotary evaporator under vacuum and chromatographs the viscous residue on silica gel (Merck Art. 7733, silica gel 60, grain size 0.2 to 0.5 mm.).

Chromatograph

Silica gel, 2 kg., are mixed with chloroform/methanol/25% ammonia (200/15/1 in vol.) and filled into a chromatography column. One dissolve the viscous oil in 800 ml. of above solvent mixture and applies the crude product to the column (insoluble components are previously filtered off). One elutes with elution agents of increasing polarity until the impurities are washed out. The product is finally eluted with chloroform/methanol/25% ammonia (50/50/5 in vol.). The combined eluates are rotary evaporated and the residual water removed with toluene. The residue is taken up in 600 ml. dichloromethane and mixed with 4 l. of acetone. The crystals which separate out at $-20°$ C. are washed with cold acetone, then with pentane and dried in a vacuum. The yield of pure hexadecylphosphocholine amounts of 250 g. (about 70% referred to hexadecylglycerol).

| Microanalysis (M.W. 407.58) | | | | |
|---|---|---|---|---|
|  | C | H | N | P |
| calc. (%): | 59.27 | 11.37 | 3.29 | 7.28 |
| found (%): | 58.98 | 11.31 | 3.21 | 7.11 |

Examples for pharmaceutical compositions

Example for a solution:

25 g. 1-n-propoxy-2,3-propanediol, 12.5 g, 1-n-hexyloxy-2,3-propanediol, 12.5 g. 1-n-nonyloxy-2,3-propanediol, 44 g. water and 1 g. phenoxyethanol are mixed and 5 g. hexadecylphosphocholine dissolved in this mixture. The solution is freed from visible particles by filtration over a suitable filter.

1 g. of solution contains 50 mg. hexadecylphosphocholine.

Example for a salve:

5 g. of substance hexadecylphosphocholine are suspended in 35 g. very viscous paraffin, 30 g. emulsifying cetyl stearyl alcohol and 30 g. white vaseline are added thereto and melted. This melt is stirred until cold. A homogeneous active material distribution is achieved by working up of the cooled melt by means of a suitable homogenisation apparatus (for example a three-roll mill).

1 g. of the hydrophilic salt contains 50 mg. hexadecylphosphocholine.

Example for an emulsion:

11.83 g. 1-n-propyloxy-2,3-propanediol, 5.91 g. 1-n-hexyloxy-2,3-propanediol, 5.91 g. 1-n-nonyloxy-2,3-propanediol, 20.35 g. water and 1.0 g. phenoxyethanol are mixed and 5 g. hexadecylphosphocholine dissolved in this mixture. On a waterbath, 30 g. white vaseline, 15 g. cetyl alcohol and 5 g. sorbitan monopalmitate are melted, heated to 70° C. and the active material solution, also heated to 70° C., emulsified in the fat phase with the help of a high-speed dispersion apparatus. Subsequently, the cream is cooled to 30° C. while stirring.

1 g. of water-in-oil cream contains 50 mg. hexadecylphosphocholine.

Example for capsules:

1.25 kg. hexadecylphosphocholine are dissolved in 5 kg. chloroform and 1.25 kg. Aerosil suspended in this solution. Subsequently, the solvent is stripped off in a vacuum. The dry mass is passed through a 1 mm. sieve and again dried in a vacuum at 30° C. in order to remove last residues of solvent. This granulate is filled in known manner on a suitable capsuling machine into hard gelatine capsules of the size 00 in an amount of 500 mg.

One capsule contains 250 mg. hexadecylphosphocholine.

Example for a lyophilisate:

In 3 liters of water for injection purposes are dissolved, with nitrogen gassing, 500 g. mannitol, 50 g. hexadecylphosphocholine are dispersed with the help of a high-speed homogenising apparatus and made up to 4 liters with water for injection purposes. This milky dispersion is converted into a slightly opalescing, colloid-disperse system by ultrasonic treatment or with the help of a slot homogeniser.

Under aseptic conditions, it is now sterile filtered over a membrane filter of 0.22 μm. pore width and filled in 40 ml. amounts into 100 ml. injection bottles with nitrogen gassing. One provides the bottles with freeze-drying stoppers and lyophilises in a suitable plant. After the drying, it is gassed with sterile, dry nitrogen and the bottles closed in the plant. The stoppers are secured with a flanged cap.

For intravenous use, the lyophilisate is reconstituted in 100 ml. water for injection purposes. 1 Bottle contains 500 mg. hexadecylphosphocholine.

I claim:

1. Composition useful in treating cancer comprising a therapeutically effective amount of hexadecylphosphocholine and an alkylglycerol of the formula

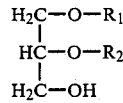

wherein one of $R_1$ and $R_2$ is an alkyl group with 2 to 12 C-atoms and the other radical an H-atom.

2. Composition of claim 1, comprising an alkylglycerol mixture of nonyl- or octylglycerol, hexyl- or pentylglycerol and propyl- or ethylglycerol.

3. Composition of claim 1, comprising from 5 to 2000 mg. hexadecylphosphocholine.

4. Composition of claim 1, comprising 5 to 200 mg. of hexadecylphosphocholine per ml. of alkylglycerol.

5. Composition of claim 1, comprising between 5 and 100 mg. of hexadecylphosphocholine.

6. Method for treating a cancer selected from the group consisting of mammary carcinoma and leukemia comprising administering to a patient with one of said cancers a therapeutically effective amount of a composition containing hexadecylphosphocholine and at least one alkylglycerol of formula

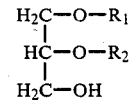

wherein one of $R_1$ and $R_2$ is an alkyl group with 2 to 12 C-atoms and the other radical is an H atom.

7. Method of claim 6, wherein said composition contains a mixture of nonyl or octylglycerol, hexyl or pentylglycerol, and propyl or ethylglycerol.

8. Method of claim 6, wherein said composition contains 5 to 2000 mg. hexadecylphosphocholine.

9. Method of claim 6, wherein said composition contains from 5 to 200 mg. hexadecylphosphocholine per ml. or alkylglycerol.

10. Method of claim 6, wherein said composition is administered in a drinking solution.

11. Method of claim 10, wherein said solution contains from 5 to 100 mg. of composition per kilogram of body weight of the patient to which said solution is administered.

12. Method of claim 6, wherein said composition is administered in intravenous form.

13. Method of claim 12, wherein said composition is administered at a dosage of from 5 to 100 mg. per kilogram of body weight of the patient to which it is administered.

* * * * *